United States Patent [19]

Hugo et al.

[11] Patent Number: 4,591,645
[45] Date of Patent: May 27, 1986

[54] PROCESS FOR THE PRODUCTION OF 2-(HYDROCARBYLDITHIO)-5-MERCAPTO-1,3,4-THIADIAZOLES

[75] Inventors: Peter Hugo; Rainer Noack, both of Berlin, Fed. Rep. of Germany

[73] Assignee: Rhein-Chemie Rheinau GmbH, Mannheim, Fed. Rep. of Germany

[21] Appl. No.: 640,614

[22] Filed: Aug. 14, 1984

[30] Foreign Application Priority Data

Aug. 27, 1983 [DE] Fed. Rep. of Germany ....... 3330920

[51] Int. Cl.$^4$ ............................................. C07D 285/12
[52] U.S. Cl. ...................................... 548/142; 548/126
[58] Field of Search ................... 548/142, 126; 568/26

[56] References Cited

U.S. PATENT DOCUMENTS 3,087,932 4/1963 Little, Jr. ............................. 260/302
3,633,561 5/1972 Blaha ............................. 260/302 SD
3,840,549 10/1974 Blaha et al. ......................... 548/142

FOREIGN PATENT DOCUMENTS 2340875 2/1974 Fed. Rep. of Germany .
1377433 12/1974 United Kingdom ................ 548/142

OTHER PUBLICATIONS

R. W. Watson in the Compendium of the 4th Gemeinschaftstagung OGEW/DGMK 1976, Salzburg, 886.
E. Blaha, Chem. Abstracts 80:3528r (1974).

Primary Examiner—Donald G. Daus
Assistant Examiner—Mary E. Ceperley
Attorney, Agent, or Firm—Connolly and Hutz

[57] ABSTRACT

2-(Hydrocarbyldithio)-5-mercapto-1,3,4-thiadiazoles are obtained by reacting bis-(2,5-dithio-1,3,4-thiadiazole with a tert.-hydrocarbyl mercaptan of which the hydrocarbyl moiety contains from 4 to 60 carbon atoms.

3 Claims, No Drawings

PROCESS FOR THE PRODUCTION OF 2-(HYDROCARBYLDITHIO)-5-MERCAPTO-1,3,4-THIADIAZOLES

This invention relates to a process for the production of 2-(tert.-hydrocarbyldithio)-5-mercapto1,3,4-thiadiazoles, hereinafter referred to as HMTD, by reacting bis-(2,5-dithio-1,3,4-thiadiazole), hereinafter referred to as BDTD, and mercaptans in accordance with the following reaction equation

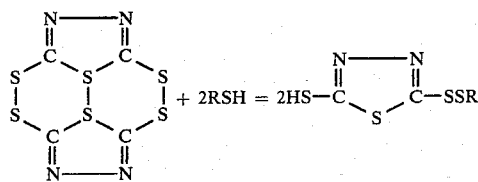

in which R represents a tert.-hydrocarbon radical containing from 4 to 60 carbon atoms.

Compounds of the HMTD type are extremely effective in inhibiting the corrosion of nonferrous metals by active sulfur (R. W. WATSON in the Compendium of the 4th Gemeinschaftstagung OGEW/DGMK 1976, Salzburg, 886; U.S. Pat. No. 3,663,561).

There are two known processes for the production of HMTD compounds.

The first process is based on the exchange of thiohydrocarbyl between 2,5-bis(hydrocarbyldithio)-1,3,4-thiadiazole, hereinafter referred to as BHDTD, and 2,5-dimercapto-1,3,4-thiadiazole, hereinafter referred to as DMTD (De-OS No. 23 40 875).

The second process is based on the oxidative coupling of DMTD and mercaptans with hydrogen peroxide in a multiphase reaction (U.S. Pat. No. 3,663,561).

The disadvantage of the first process lies in the use of BHDTD, of which the production involves considerable expense (U.S. Pat. No. 3,087,932).

The disadvantage of the second process lies in the immiscibility of DMTD and the mercaptan used on the one hand and the aqueous solution of hydrogen peroxide on the other hand. The reaction which thus takes place in three phases necessitates intensive mixing and, in some cases, the addition of solvents. Another disadvantage is that pure HMTD can be obtained from the reaction mixture only by carrying out an extraction process.

The object of the present invention was to provide a process for the production of HMTD which does not have any of the disadvantages referred to previously.

According to the invention, this object is achieved by reacting BDTD with a mercaptan corresponding to the following formula:

RSH in which R represents a tertiary hydrocarbon radical containing from 4 to 60 carbon atoms.

The reaction is preferably carried out at temperatures in the range from 20° to 150° C., the BDTD and the mercaptan being reacted in a molar ratio of 1:2, more particularly in the absence of any reaction auxiliaries.

The hydrocarbon radical may be saturated or unsaturated, but is preferably saturated.

The tertiary carbon atom is directly attached to the sulfur atom. The carbon chain may contain further tertiary carbon atoms, i.e. it may be further branched.

R preferably contains from 8 to 20 carbon atoms. Instead of using pure mercaptan, it is also possible to use technical mixtures.

The production process according to the invention is based on readily obtainable starting materials. Tertiary mercaptans are commercially available products. BDTD is formed from DMTD by oxidation using $H_2O_2$ in the absence of other reactants.

The process according to the invention, including the synthesis of BDTD, comprises two stages whereas the process according to U.S. Pat. No. 3,663,561 is a single-stage process, the structures of any intermediate stages formed being unknown.

The advantage of the process according to the invention with its two separate stages lies in the fact that, in both stages, the products formed, namely BDTD and HMTD, are pure and do not need any further working up. In the single-stage process, the reaction mixture has to be worked up by an elaborate procedure.

The following methods are used for assessing the reaction and the product:

In contrast to the mercaptan used and to HMTD, BDTD is completely insoluble in dioxane.

The conversion may be determined by diluting product samples with dioxane in a ratio of 1:10, filtering the samples thus diluted and gravimetrically determining the dried residue.

The composition of the filtrate is then determined by high pressure liquid chromatography. Using a Waters CN-column 25 cm long and an eluent of 99% by volume of n-heptane and 1% by volume of n-octonal, the tert.-mercaptan used, HMTD and any secondary products formed are separated from one another at a flow rate of 2 ml/minute. For quantitative evaluation, the signals of a UV-detector calibrated beforehand with the pure substances are evaluated. The substances are identified from the retention time.

EXAMPLE 1

40 g (0.2 mole) of tert.-dodecyl mercaptan and 30 g (0.1 mole) of powdered BDTD were stirred at room temperature to form a paste. The mixture thus prepared was then left standing for 2 hours at 100° C. in a drying cabinet. A weight check before and after the reaction in the drying cabinet did not reveal any measurable weight loss.

The yellow, viscous liquid product obtained after cooling at room temperature was analyzed in the same way as described above. The results are shown in Table 1.

In addition, an osmometric molecular weight determination was carried out and, at M=346 g/mole, produced virtually the theoretical value (350.6 g/mole).

In order to show that the reaction according to the invention takes place in a molar ratio of 1:2 between BDTD and the tertiary mercaptan, reactions with an excess of one of the components were carried out in Examples 2 and 3 below.

EXAMPLE 2

40 g (0.2 mole) of tert.-dodecyl mercaptan and 36 g (0.12 mole) of powdered BDTD were stirred at room temperature to form a paste and further processed in the same way as described in Example 1.

The yellow product mixture which still contained solids after cooling at room temperature was analyzed in the same way as described above. The data are shown in Table 1.

EXAMPLE 3

80 g (0.4 mole) of tert.-dodecyl mercaptan and 30 g (0.1 mole) of powdered BDTD were stirred at room temperature to form a paste and further processed in the same way as in Example 1.

The yellow, liquid product mixture obtained after cooling at room temperature was analyzed in the same way as described above. The data are shown in Table 1.

EXAMPLE 4

32 g (0.2 mole) of tert.-nonyl mercaptan and 30 g (0.1 mole) of powdered BDTD were stirred at room temperature to form a paste. The mixture thus prepared was left standing for 2 hours at 80° C. in a drying cabinet. A weight check before and after the reaction in the drying cabinet did not reveal any measurable weight loss. The yellow, solid product obtained after cooling was analyzed in the same way as described above. The results are shown in Table 1.

TABLE 1

Analytical data of the product mixtures obtained in Examples 1 to 4

| Example No. | Conversion BDTD gravimetric | Chromatographic analysis of the dioxane solution | | |
|---|---|---|---|---|
| | | HMTD (mole %) | Mercaptan (mole %) | Other components |
| 1 | 98% | 98 | 2 | traces |
| 2 | 82% | 98 | 2 | traces |
| 3 | 100% | 50 | 50 | traces |

TABLE 1-continued

Analytical data of the product mixtures obtained in Examples 1 to 4

| Example No. | Conversion BDTD gravimetric | Chromatographic analysis of the dioxane solution | | |
|---|---|---|---|---|
| | | HMTD (mole %) | Mercaptan (mole %) | Other components |
| 4 | 98% | 98 | 2 | traces |

EXAMPLE 5

15 g of DMTD (0.1 mole) in the form of a powder having a particle diameter of less than 0.5 mm are suspended in 200 ml of water at 20° C. 12 g of a 35% hydrogen peroxide solution (corresponding to 0.1 mole) are added with vigorous stirring at such a rate that the reaction temperature does not exceed 50° C. One hour after addition of the hydrogen peroxide, the BDTD formed as a white deposit is filtered off and dried. At 15 g (0.05 mole) the yield is quantitative.

We claim:

1. A process for the production of compounds corresponding to the following formula:

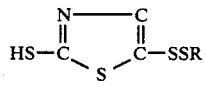

in which R represents a tertiary hydrocarbon radical containing from 4 to 60 carbon atoms, characterized in that bis-(2,5-dithio-1,3,4-thiadiazole) is reacted with a compound corresponding to the formula:

R—SH in which R is as defined above.

2. A process as claimed in claim 1, characterized in that the reaction is carried out at a temperature of from 20° to 150° C. and with a molar ratio of bis-(2,5-dithio-1,3,4-thiadiazole) to mercaptan RSH of 1:2.

3. A process as claimed in claim 2, characterized in that tert.-dodecyl mercaptan is used as the mercaptan.

* * * * *